United States Patent
Beling et al.

(10) Patent No.: US 8,092,435 B2
(45) Date of Patent: Jan. 10, 2012

(54) PORTAL WITH SEPTUM EMBEDDED INDICIA

(75) Inventors: William Lloyd Beling, New Brighton, MN (US); Kristin Finberg, Minneapolis, MN (US); Ronald Gene Travis, Spring Lake Park, MN (US)

(73) Assignee: Smiths Medical ASD, Inc., Rockland, MA (US)

( * ) Notice: Subject to any disclaimer, the term of this patent is extended or adjusted under 35 U.S.C. 154(b) by 0 days.

(21) Appl. No.: 12/588,473

(22) Filed: Oct. 16, 2009

(65) Prior Publication Data

US 2011/0092921 A1    Apr. 21, 2011

(51) Int. Cl.
*A61M 37/00* (2006.01)

(52) U.S. Cl. .................................. 604/288.02

(58) Field of Classification Search .................. 604/175, 604/288.01, 288.02; 600/424
See application file for complete search history.

(56) References Cited

U.S. PATENT DOCUMENTS

| | | | |
|---|---|---|---|
| 4,863,470 A * | 9/1989 | Carter ............................... 623/8 |
| 5,558,641 A * | 9/1996 | Glantz et al. .............. 604/288.02 |
| 5,562,618 A * | 10/1996 | Cai et al. ................... 604/288.02 |
| 5,613,945 A * | 3/1997 | Cai et al. ................... 604/288.02 |
| 5,743,873 A * | 4/1998 | Cai et al. ................... 604/288.02 |
| 5,989,216 A * | 11/1999 | Johnson et al. ........... 604/288.02 |
| 2005/0124980 A1 | 6/2005 | Sanders |
| 2006/0224129 A1 | 10/2006 | Beasley et al. |
| 2006/0247584 A1 | 11/2006 | Sheetz et al. |
| 2006/0264898 A1 | 11/2006 | Beasley et al. |
| 2007/0233017 A1 | 10/2007 | Zinn et al. |
| 2007/0276344 A1 | 11/2007 | Bizup et al. |
| 2008/0140025 A1 | 6/2008 | Sheetz et al. |
| 2008/0208236 A1 | 8/2008 | Hobbs et al. |
| 2008/0319399 A1 | 12/2008 | Schweikert et al. |
| 2009/0024024 A1 | 1/2009 | Zinn |
| 2009/0156928 A1* | 6/2009 | Evans et al. .................... 600/424 |
| 2009/0204072 A1* | 8/2009 | Amin et al. .................... 604/116 |
| 2009/0227862 A1 | 9/2009 | Smith et al. |
| 2010/0063451 A1* | 3/2010 | Gray et al. ..................... 604/175 |
| 2010/0069743 A1* | 3/2010 | Sheetz et al. ................... 600/424 |
| 2010/0268165 A1* | 10/2010 | Maniar et al. .................. 604/175 |

* cited by examiner

*Primary Examiner* — Nicholas Lucchesi
*Assistant Examiner* — Aarti B Berdichevsky
(74) *Attorney, Agent, or Firm* — Louis Woo

(57) ABSTRACT

An implantable portal includes a septum that has embedded therein an indicia adapted to identify at least one characteristic of the portal. The indicia may be formed as an impression at a base layer of the septum, and is filled with a radiopaque material. The septum base layer is covered by liquid silicone, which bonds with the septum base layer when solidified, so that an integral one-piece septum, with the identifier indicia embedded therein, is effected. The indicia embedded septum is fitted to the reservoir housing of the portal for providing identification information for that portal. The septum embedded indicia is viewable visually and also by x-ray or computer tomography imaging.

16 Claims, 5 Drawing Sheets

SECTION A-A

PORTAL WITH SEPTUM EMBEDDED INDICIA

FIELD OF THE INVENTION

The instant invention relates to implantable medical devices and more particularly to a portal that can readily be identified after being implanted into a patient.

BACKGROUND OF THE INVENTION

The portal of the instant invention is a subcutaneous implantable access device that includes a reservoir and a septum through which fluid may be input or removed from the reservoir. Such subcutaneous implantable device is known and is commonly referred to as a port or portal, and is exemplified by the following patents assigned to the same assignee as the instant application: U.S. Pat. Nos. 5,558,641, 5,562,618, 5,613,945, 5,743,873 and 5,989,216. The respective disclosures of the '641, '618, '945, '873 and '216 patents are incorporated by reference to the disclosure of the instant application. Such portals are implanted into patients, with the self resealable septums of the portals providing access to the reservoirs so that fluid medicaments and other infusate fluids may be stored in the reservoirs for infusing to the patients. Instead of storing medication to be infused to the patient, patient fluid such as blood may be withdrawn from the reservoir, by using for example a cannula or needle.

For portals that have been implanted into patients, oftentimes it is necessary to determine given properties or characteristics of those portals, for example determining whether a certain portal is adaptable to be used for power injection. Accordingly, it is desirable that some indicia be provided to a portal so that even after the portal has been implanted into a patient, the particular characteristic(s) or property(s) of the portal can be ascertained.

There are a number of implantable portals that have an identifier that is discernable by x-ray or palpations. These portals are disclosed in U.S. patent publication Nos. 2009/0024024, 2007/0276344, 2005/0124980, 2006/0224129 and 2008/0319399. The portals disclosed in the noted patent publications either have septums that have protuberances formed at its outer surface so that the portals may be palpated by the user over the skin of the patient, or have identifiers etched to the body of the portals that are x-ray viewable.

BRIEF SUMMARY OF THE INVENTION

The instant invention portal provides an efficient and economic way of arranging an identifier or indicia at the portal so that particular characteristics of the portal may be easily discerned, either visually, or by x-ray and/or computer tomography imaging when the portal is implanted in a patient.

In particular, the septum of the instant invention comprises an elastomeric silicone rubber that forms the base, or base layer, of the septum. The septum base may be formed by molding, with the outlines of an identification indicia or marking being formed during the molding process. The indicia may be in the form of an impression, or impressions, adapted to convey information identifying a particular characteristic or property, or given characteristics or properties, of the portal. To enhance visibility, the impression(s) is filled with a radiopaque material such as for example barium sulfate (BaSO4). After the molded impression is filled with the radiopaque material, liquid silicone is injected onto the top surface of the septum base where the identification impression is formed. When solidified or hardened, the liquid silicone bonds to and becomes an integral part of the silicone septum base so that the end product septum is a one piece unitary integral septum that has embedded therein the radiopaque material configured by the impression as an identification indicia adapted to convey information relating to at least one characteristic of the portal. As the identification indicia is embedded in the septum, it is not affected by the environment. Also, as the liquid silicone injected to cover the top surface of the silicone base is clear, a user such as a surgeon or other medical personnel can visually view the indicia to identify the portal, when the portal is viewable visually. When a portal has been implanted in a patient, due to the radiopaque quality of the identification indicia embedded in the septum, the indicia can readily be discernable by either x-ray or computer tomography imaging.

The indicia embedded septum of the instant invention may be manufactured with different types of portals, including multiple reservoir portals, portals that have plastic housings and portals that are made entirely from titanium or other patient friendly metals or materials.

BRIEF DESCRIPTION OF THE FIGURES

The present invention will become apparent and the invention itself will be best understood with reference to the following description of the present invention taken in conjunction with the accompanying drawings, wherein.

DETAILED DESCRIPTION OF THE INVENTION

Figure 1:
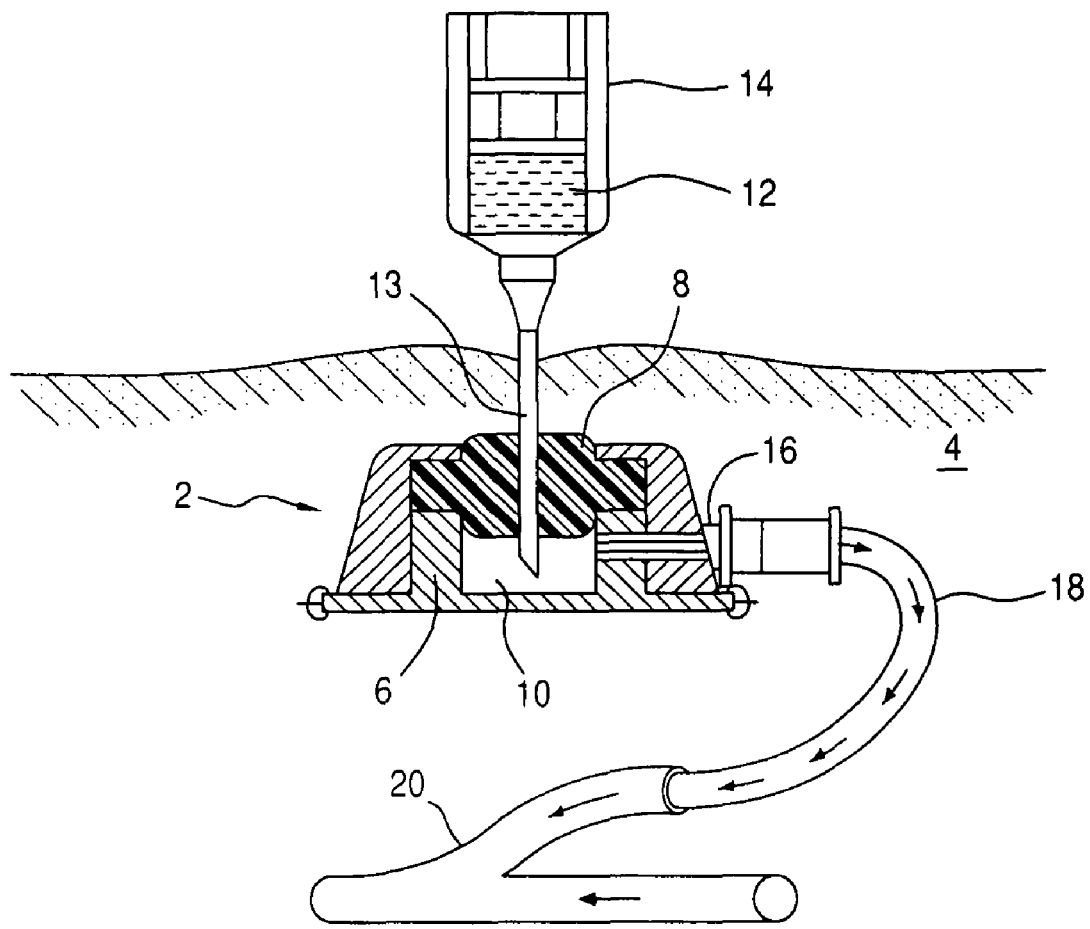
FIG. 1 is a view of a prior art portal implanted into a patient.

With reference to FIG. 1, a portal 2, such as for example that disclosed in the aforementioned U.S. Pat. No. 5,558,641, is shown to have been implanted in a patient 4. Portal 2 has a housing 6 covered by a self resealable elastomeric rubber septum 8 such that a reservoir 10 is formed in housing 6 for accepting a liquid medicament 12 from a syringe or an injection pump 14. An outlet 16 at housing 6 is connected to a catheter 18, which routes the liquid medicament from reservoir 10 to a vein 20 of patient 4.

Given that the portal is subcutaneously implanted in the patient, to fill or replenish the medicament in reservoir 10, the user has to locate the portal, and specifically septum 8 so that septum 8 may be pierced by needle 13 for inputting the liquid medicament to reservoir 10. One method of locating the portal is by palpation. To enable a user to feel the portal, tactile protrusions are provided at the top surface of the septum. However, palpation oftentimes does not accurately determine the location of the portal. Moreover, having protrusions at the septum of the portal may in practice adversely affect the piercing of the septum since the top surface of the septum is not smooth.

Another method by which the location of the portal within the patient may be ascertained is by radiographic imaging using x-ray or computer tomography. For radiographic imaging, the prior art portals have etched at their housings markings that appear under x-ray or computer tomography. However, such etching or markings at the housing, although may identify the location of the portal, do not provide in a simple and straight forward manner the accurate location of the septum where the needle has to be inserted. Moreover, the portal may move or shift within the patient, so that the location of the septum of the portal may not be readily determined at all times.

Figure 2:
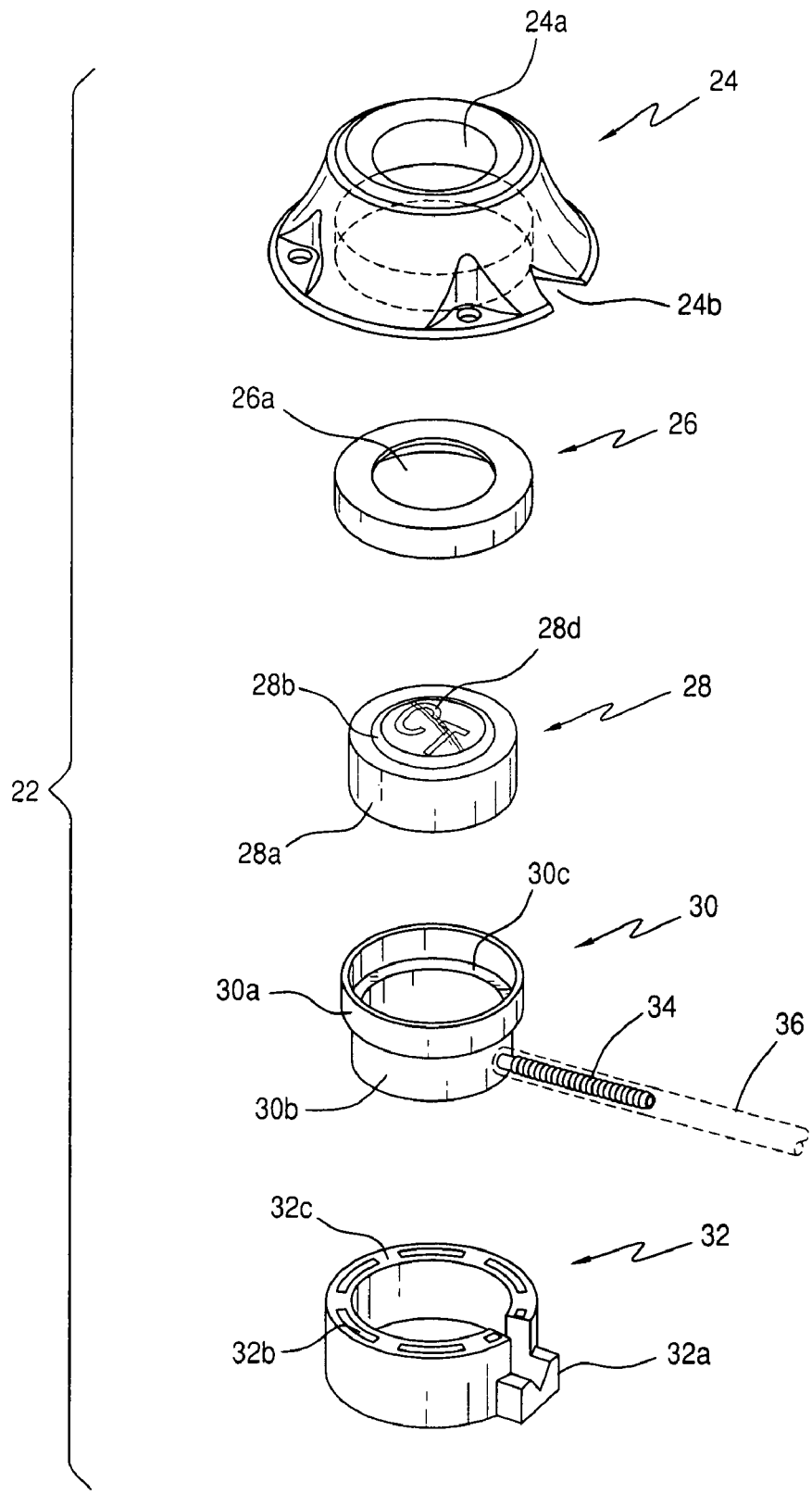
FIG. 2 is a disassembled view of the subcutaneous implantable portal of the instant invention.

With reference to FIG. 2, a disassembled view of the various components or elements of the portal of the instant invention is shown. In particular, portal 22 includes a housing 24, a cap 26, a septum 28, a reservoir body 30 and a housing base 32. Reservoir body 30 is cup-shaped and is shown to have an upper portion 30a and a lower portion 30b, which includes the base of the reservoir body 30. A shoulder 30c joins upper portion 30a to lower portion 30b. An outlet 34 extends from lower portion 30b of reservoir body 30. A conduit or catheter 36, in phantom line, is connected to outlet 34 for transporting fluid stored in reservoir body 30 to a selected location within a patient, when portal 22 is implanted subcutaneously in the patient.

Figure 3:
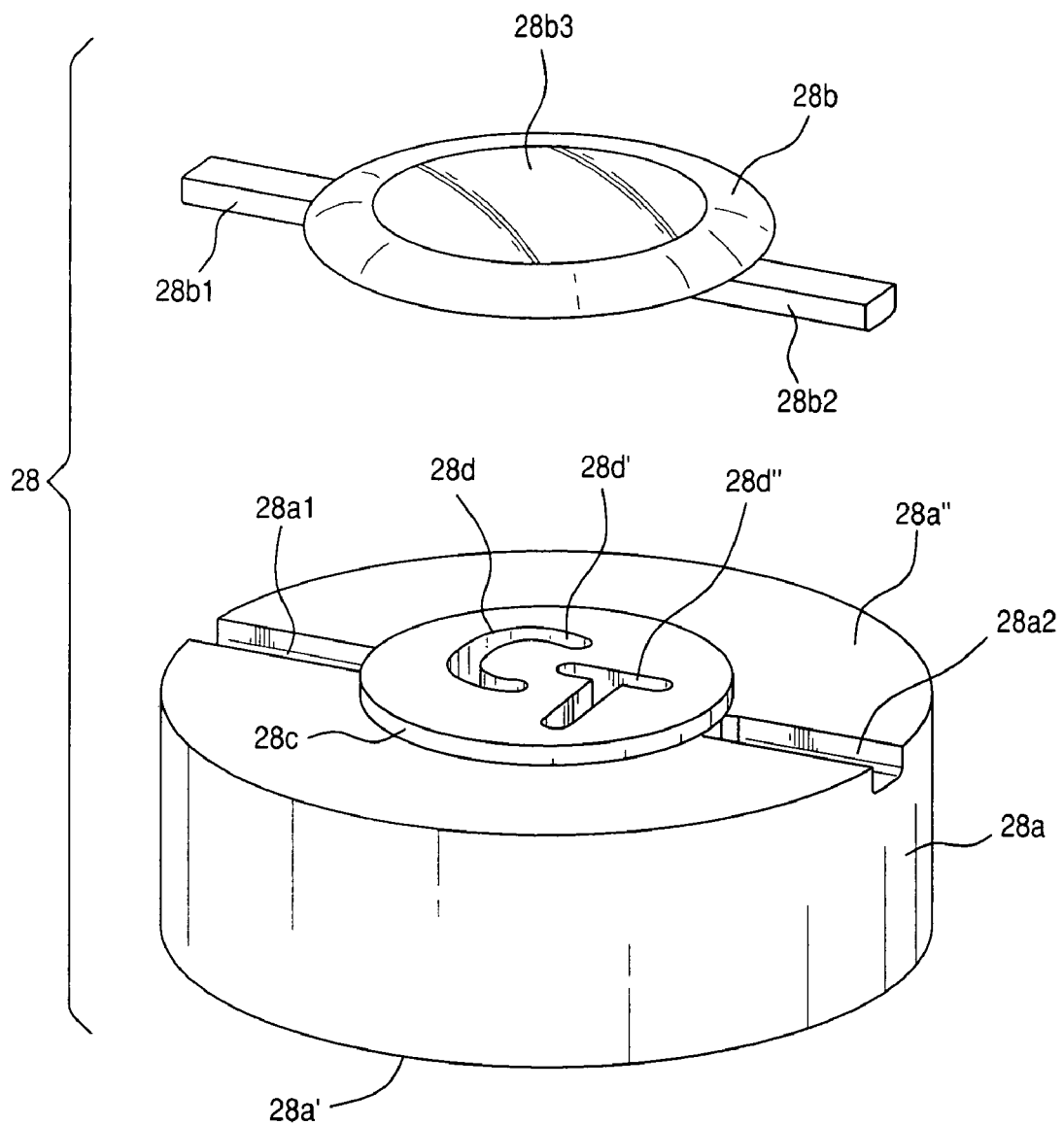
FIG. 3 shows the septum of the instant invention portal, with the inventive septum being separated into two layers—a base layer and a cover layer—for the purpose of discussion.

Fitted to the upper portion 30a of reservoir body 30, with shoulder 30c providing a rest stop therefore, is septum 28. As shown, septum 28 is a one piece integral unitary component that in fact is made in multiple steps and may be illustrated as comprising two septum layers 28a and 28b, per illustrated in FIG. 3. Septum layer 28a, also referred herein as the septum base layer, may be made from a silicone gum stock or LIM (liquid injection molding) material, for example. Septum base layer 28a is fabricated to have to have a thickness and a cross-section that enable at least the lower portion of it to be form fitted to upper portion 30a of reservoir body 30. Septum base layer 28a is molded to have a flat bottom surface 28a' and a top surface 28a" that includes two channels 28a1 and 28a2. Septum layer 28a may further be molded to have a raised layer 28c with a particular impression, mark or marking 28d configured as an identification indicia to convey information to a user. For the FIG. 3 exemplar septum, information conveying impression 28d is shown to include the letters "CT", formed as depressions or channels 28d' and 28d" in raised layer 28c. Instead of being formed in a raised layer, impression 28d may be formed directly on surface 28a" of silicone layer 28a, without any raised layer.

As the silicone material from which septum 28 is made is transparent, septum 28 itself is transparent. To ensure that impression 28d may be view visually (with the naked eye), channels 28d' and 28d" are filled with a non-transparent or opaque material. When portal 22 is not viewable visually or when the portal has been implanted in a patient, so that impression 28d may be viewed under radiographic imaging such as x-ray or computer tomography, channels 28d' and 29d" are filled with a radiopaque material such as barium sulfate (BaSO4), or some other similar radiopaque material viewable under radiographic imaging.

An upper septum layer 28b—which may also be referred to as the septum top, sealant or cover layer—superposes over septum base layer 28a to cover at least the latter's raised layer 28c. A pair of arms 28b1 and 28b2 of septum cover layer 28b are correspondingly fitted to channels 28a1 and 28a2 formed at septum base layer 28a. Due to the transparency of the silicone elastomeric material, septum cover layer 28b presents a clear window 28b3 over marking 28d, so that the impression "CT" may be viewed visually.

Although shown as a separate layer from septum base layer 28a, in actuality, septum cover layer 28b is injected or deposited as a liquid silicone onto top surface 28a" of septum base layer 28a so that the liquid silicone fills channels 28a1 and 28a2, as well as covers and/or seals raised layer 28c including impression channels 28d' and 28d" filled with the radiopaque material. When hardened or solidified, silicone cover layer 28b bonds to base layer 28a and in fact becomes an integral part of silicone base layer 28a, so that end product septum 28 is an integral one-piece unitary component, with the identification indicia, for example "CT", embedded therein.

As noted above, to provide visibility when the portal has been implanted subcutaneously in a patient, the impression channels 28d' and 29d" are filled with a radiopaque material such as barium sulfate (BaSO4), before top surface 28a" of septum base layer 28a is covered by the injected liquid silicone that forms septum cover layer 28b. With impression 28d in septum base layer 28a having been filled with a radiopaque material, impression 28d can readily be discerned by either x-ray or computer tomography (CT) imaging. To convey at least one property or characteristic of the portal to which septum 28 is fitted, impression 28d may be formed or configured as letter(s), character(s), number(s), combinations thereof, or some other identifying indicia. By covering raised portion 28c with the clear cover layer 28b, septum 28 is devoid of any protrusions at its upper surface, and therefore would not affect the piercing thereof by the sharp end of a needle or cannula, as was discussed above with respect to septums that have tactile protrusions formed on their outer surfaces.

Figure 4A:
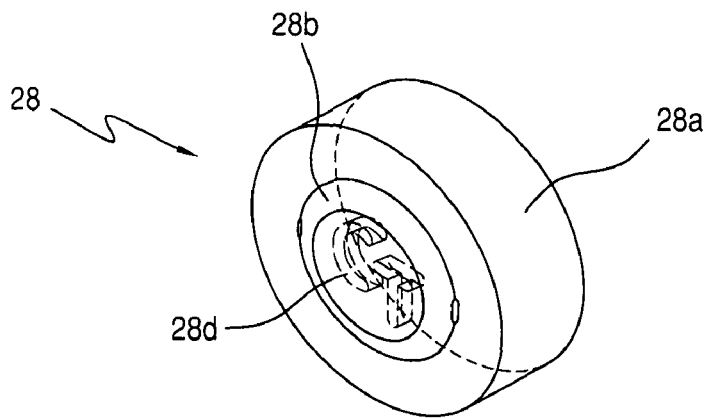
FIGS. 4a-4c are respective views of the inventive septum of the portal of the instant invention.
Figure 4B:
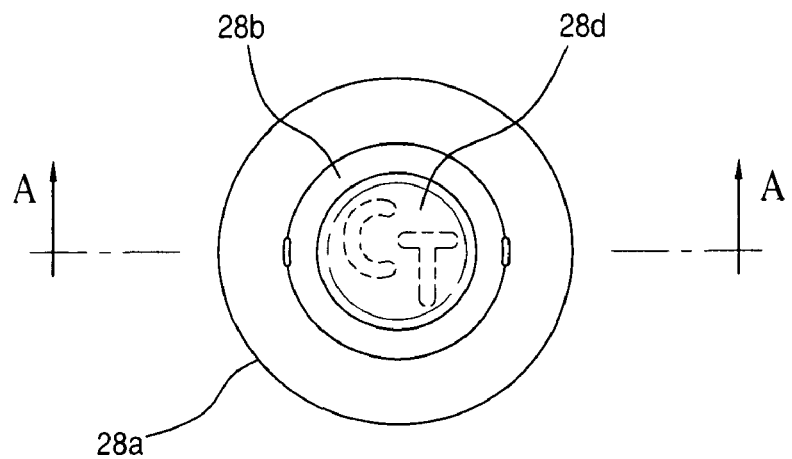
Figure 4C:
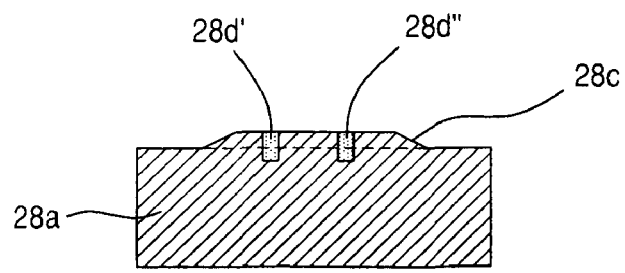

FIGS. 4a and 4b are the perspective view and plan view, respectively, of the completely formed inventive septum 28. FIG. 4c is a cross-sectional view of the inventive septum showing the radiopaque material having filled channels 28d' and 28d" of marking 28d at raised layer 28c. The characteristics or properties conveyed by marking 28d may identify the portal to which the septum is fitted as being able to support power injection, or some other usage. The radiopaque marking 28d readily enables the viewing of the indicia under x-ray or computer tomography imaging, when the portal has been implanted subcutaneously in the patient.

Returning to FIG. 2, once septum 28 is fitted to the upper portion 30a of reservoir body 30, to hold septum 28 in place, a cap 26 is friction fitted over top portion 30a of reservoir body 30. For the exemplar portal embodiment of FIG. 2, both cap 26 and reservoir body 30 are made from titanium, or some other inert metal acceptable for implantation to a patient. An opening 26a at cap 26 exposes marking 28d embedded in septum 28. The assembled reservoir housing—made up of reservoir body 30, septum 28 and cap 26—is then be placed in housing base 32. Housing base 32 is in the form of a collar with its inside diameter having a dimension sufficient to receive reservoir body 30, and a notched support 32a at a side thereof for accepting outlet 34. Housing 24 is then positioned over housing base 32 to envelop the assembled reservoir housing. A slot 24b at the lower portion of housing 24 provides accommodation for outlet 34 of reservoir body 30 that extends out of housing base 32 at support 32a. A top opening 24a at housing 24 exposes the top surface of septum 28, and therefore marking 28d embedded therein. To prevent separation, housing 24 and housing base 32 are ultrasound welded, possibly at the locations defined by the grooves 32b at the lip 32c of housing base 32. To save weight and cost, housing 24 and housing base 32 may be made from conventional medical plastics material.

Figure 5:
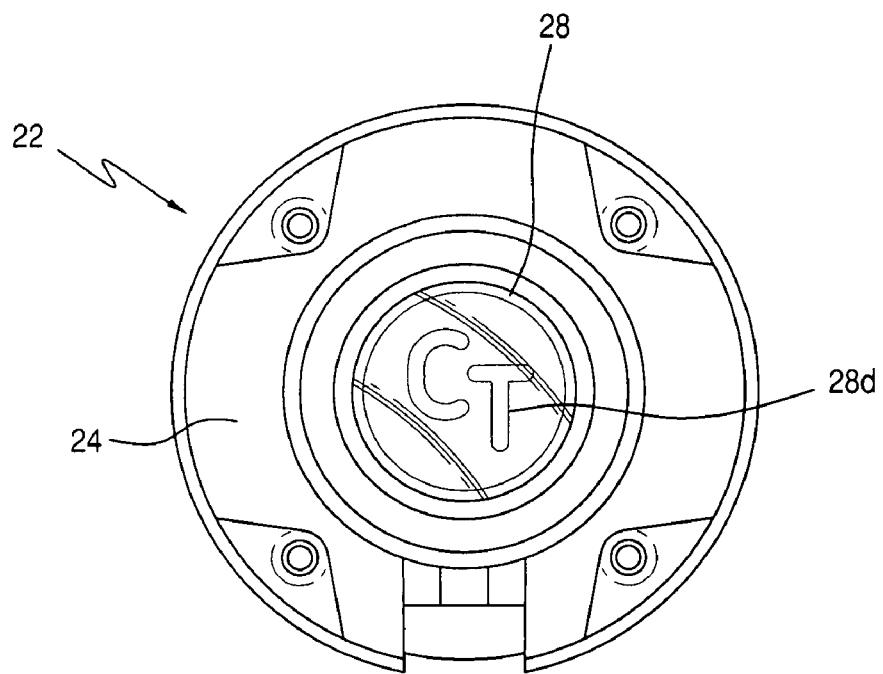
FIG. 5 is a plan view of the portal of the instant invention showing in particular the identification indicia in the inventive septum.
Figure 6A:
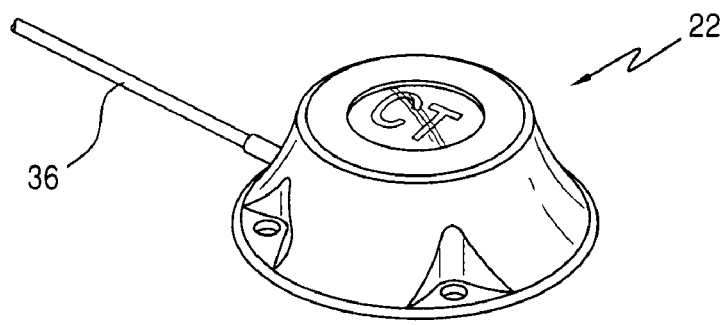
FIGS. 6a and 6b are perspective views of exemplar portals assembled with the septum of the instant invention.

A plan view of the assembled portal 22 in FIG. 5 shows visually the marking "CT" in septum 28. A perspective view of the assembled exemplar portal of FIG. 2 is shown in FIG. 6a.

Figure 6B:
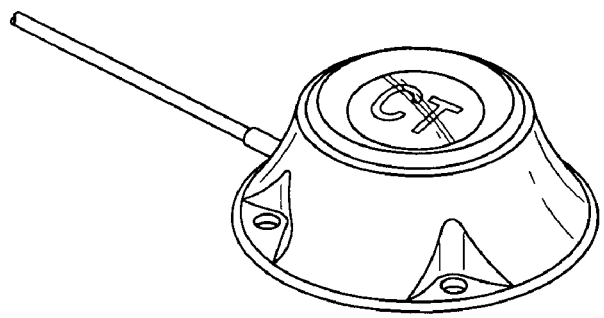

FIG. 6b shows another embodiment of the portal of the instant invention that comprises a housing that, like the reservoir body and cap of the FIG. 2 portal, are also made of titanium, so that the entire FIG. 6b portal is made of titanium, or some other similar patient friendly inert metal.

Inasmuch as the present invention is subject to many variations, modifications and changes in detail, it is intended that all matter described throughout this specification and shown in the accompanying drawings be interpreted as illustrative only and not in a limiting sense. For example, instead of a single reservoir portal, the present invention is also adapted to include dual reservoir ports such as that disclosed in the above noted U.S. Pat. No. 5,743,873. Moreover, instead of the illustrated "CT", the identifier or identification indicia embedded in the inventive septum may have other markings such as for example "PI" to illustrate that the portal is adapted for power injection. Other markings or identification means may include numbers that can convey to the viewer, by x-ray or computer tomography imaging, that the portal is of a particular dimension and can hold a given amount of fluid. For example, a "3" embedded in the septum, in addition to other markings, may indicate to the user that the reservoir has a fluid capacity of 3 ml or is of a dimension that equals to size 3 for that type of portal or port. Furthermore, even though the radiopaque material filled marking is discussed above as viewable by x-ray and computer tomography imaging, it should be appreciated that the channel(s) of the impression that outlines of the marking may be formed or molded to have a given depth or configuration able to reflect sound waves, so that the portal of the instant invention, per its inventive septum, in addition to being viewable under x-ray and computer tomography imaging, is also viewable by ultrasound.

The invention claimed is:

1. A visually identifiable port, comprising:
a housing having an opening and an outlet;
a resealable elastomeric septum having a base layer fitted to the opening of said housing to enclose a fluid reservoir inside said housing;
a catheter connect to said outlet to be in fluid communication with said reservoir; and
an identifier embedded in said septum to convey information about said port,
wherein said identifier comprises at least one impression formed on a base layer of said septum, said impression having a readable configuration.

2. Port of claim 1, wherein said identifier includes a radiopaque material visible under computer tomography and/or x-ray imaging for providing an indicia for said port.

3. Port of claim 1, wherein said at least one impression is filled with a radiopaque material and may be viewed visually.

4. Port of claim 3, wherein the radiopaque material comprises barium sulfate (BaSO4).

5. Port of claim 1, wherein said septum comprises a plurality of elastomeric layers, said identifier being formed in the base layer and covered by a clear upper layer, said base layer and said upper layer integrally bonding to each other so that said septum is an integral one piece unitary component with said identifier embedded therein.

6. Port of claim 1, wherein the readable configuration of said at least one impression is configured to convey at least one characteristic of said port, a radiopaque material filling said impression, and a sealant layer covering at least said impression filled with the radiopaque material.

7. Port of claim 6, wherein said base and sealant layers are made from silicone, wherein the radiopaque material comprises barium sulfate (BaSO4), and wherein said sealant layer is clear so that said impression is viewable visually through said sealant layer.

8. Port of claim 1, wherein the base layer of said septum is covered by a transparent upper layer that presents a clear window to said at least one impression.

9. Port of claim 8, wherein the base layer and the upper layer of said septum are bonded together so that said septum becomes an integral one-piece unitary component with said at least one impression embedded therein.

10. A port implantable in a patient for delivering infusate subcutaneously to the patient, comprising:
a housing having an opening;
a resealable septum having a base layer fitted to the opening to form a reservoir inside said housing, said septum providing access to the reservoir;
an outlet extending from said housing and in fluid communication with said reservoir;
a catheter connected to said outlet for outputting infusate stored in the reservoir; and
identification means embedded in said septum to convey information about said port,
wherein said identification means comprises an impression formed on the base layer of said septum, said impression having a readable configuration.

11. Port of claim 10, wherein said identification means includes a radiopaque material adapted to be viewed by computer tomography and/or x-ray imaging.

12. Port of claim 10, wherein said impression is filled with a radiopaque material, the surface of said base layer where said impression is formed is sealed with a clear cover layer, said base and cover layers being silicone integrally bonded to each other to form a one piece unitary septum.

13. Port of claim 10, wherein said identification means comprises a visual indicia.

14. Port of claim 10, wherein said impression is configured in alphabetic and/or numeric format to convey information relating to at least one characteristic of said port visually and/or under computer tomography or x-ray imaging when said impression is filled with a radiopaque material.

15. Port of claim 10, wherein the base layer of said septum is covered by a transparent upper layer that presents a clear window to said impression.

16. Port of claim 15, wherein the base layer and the upper layer of said septum are bonded together so that said septum becomes an integral one-piece unitary component with said impression embedded therein.

* * * * *